United States Patent
Weiner et al.

(10) Patent No.: US 10,631,902 B2
(45) Date of Patent: Apr. 28, 2020

(54) BONE SHORTENING DEVICE AND METHOD

(71) Applicant: NEXTREMITY SOLUTIONS, INC., Warsaw, IN (US)

(72) Inventors: Lon S. Weiner, Rumson, NJ (US); Stuart D. Katchis, Scarsdale, NY (US); John R. Pepper, Cheshire, CT (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 889 days.

(21) Appl. No.: 14/427,516

(22) PCT Filed: Sep. 12, 2013

(86) PCT No.: PCT/US2013/059495
§ 371 (c)(1),
(2) Date: Mar. 11, 2015

(87) PCT Pub. No.: WO2014/043370
PCT Pub. Date: Mar. 20, 2014

(65) Prior Publication Data
US 2015/0245858 A1    Sep. 3, 2015

Related U.S. Application Data

(60) Provisional application No. 61/700,050, filed on Sep. 12, 2012.

(51) Int. Cl.
*A61B 17/80* (2006.01)
*A61B 17/15* (2006.01)

(52) U.S. Cl.
CPC .............. *A61B 17/80* (2013.01); *A61B 17/15* (2013.01); *A61B 17/151* (2013.01); *A61B 17/8061* (2013.01)

(58) Field of Classification Search
CPC ...... A61B 17/80; A61B 17/8014; A61B 17/15; A61B 17/151
See application file for complete search history.

(56) References Cited

U.S. PATENT DOCUMENTS 5,042,983 A * 8/1991 Rayhack ............... A61B 17/15
606/53
5,443,516 A * 8/1995 Albrektsson ........... A61F 2/384
606/70

(Continued)

FOREIGN PATENT DOCUMENTS

CN         201617934 U    11/2010

OTHER PUBLICATIONS

International Search Report for PCT/US2013/059495 dated Dec. 3, 2013.

(Continued)

*Primary Examiner* — Bruce E Snow
*Assistant Examiner* — Melissa A Hoban
(74) *Attorney, Agent, or Firm* — Heslin Rothenberg Farley & Mesiti P.C.; Victor A. Cardona, Esq.

(57) ABSTRACT

Bone fixation devices and plates are disclosed. The bone fixation device includes a first portion, a second portion, and a third portion. The first portion includes at least one opening. The second portion includes at least one second opening. The third portion is positioned between the first portion and the second portion and is configured to guide the cutting of a bone. The bone fixation plate includes a first plate portion, a second plate portion, and a third plate portion. The first plate portion includes at least one screw hole for receiving a first bone screw. The second plate portion includes at least one slot for receiving a second bone screw. The third plate portion is positioned adjacent to the first and second plate portions and is configured to guide (Continued)

bone cutting A method of altering a bone using the bone fixation devices and plates is also disclosed.

14 Claims, 14 Drawing Sheets

(56) References Cited

U.S. PATENT DOCUMENTS

| | | | | |
|---|---|---|---|---|
| 6,007,535 | A * | 12/1999 | Rayhack | A61B 17/15 606/105 |
| 6,364,881 | B1 * | 4/2002 | Apgar | A61B 17/8085 606/280 |
| 7,540,874 | B2 | 6/2009 | Trumble et al. | |
| 8,821,551 | B2 * | 9/2014 | Zeetser | A61B 17/8033 606/281 |
| D740,943 | S * | 10/2015 | Neufeld | A61B 17/80 D24/155 |
| 9,283,008 | B2 * | 3/2016 | Gonzalez-Hernandez | A61B 17/8085 |
| 2005/0085819 | A1 * | 4/2005 | Ellis | A61B 17/8076 606/71 |
| 2005/0277941 | A1 * | 12/2005 | Trumble | A61B 17/15 606/79 |
| 2007/0270850 | A1 | 11/2007 | Geissler | |
| 2009/0210010 | A1 * | 8/2009 | Strnad | A61B 17/8014 606/280 |
| 2009/0254126 | A1 | 10/2009 | Orbay et al. | |
| 2010/0168799 | A1 | 7/2010 | Schumer | |
| 2017/0164990 | A1 * | 6/2017 | Weiner | A61B 17/809 |

OTHER PUBLICATIONS

Mar. 17, 2015: International Preliminary Report on Patentability for International Application No. PCT/US2013/059495.
Communication issued by the European Patent Office in connection with European Patnet Application No. 13771667.6 dated Dec. 6, 2016.

* cited by examiner

BONE SHORTENING DEVICE AND METHOD

CROSS-REFERENCE TO RELATED APPLICATIONS

This application is a National Stage application based on International Application PCT/US2013/059495 filed on Sep. 12, 2013, published as WO 2014/043370 A1 on Mar. 20, 2014. This application also claims priority benefit of U.S. provisional application No. 61/700,050 filed Sep. 12, 2012, which are incorporated herein by reference.

FIELD OF THE INVENTION

The present disclosure relates to corrective surgery and bone fixation.

BACKGROUND OF THE INVENTION

Bone shortening procedures are used to treat patients or individuals having one bone longer than a corresponding bone. For example, if a patient's left leg or right leg is longer than the other due to a corresponding bone being longer. Bone shortening requires complex surgical procedures which may result in complications when bones are of an irregular shape or when certain shape bones require a longer recovery period. Bone plates used to affix to the bone in a shortening procedure are typically ill equipped for various scenarios and are not ideal for helping a practitioner or surgeon determine where cuts in the bone are to be made in a shortening procedure.

SUMMARY OF THE INVENTION

Aspects of the present disclosure provide bone fixation devices, bone fixation plates, and methods for performing a bone fusion. In one aspect, provided herein is a bone fixation device, including a first portion with at least one first opening, a second portion with at least one second opening, and a third portion positioned between the first portion and the second portion. The third portion configured to guide the cutting of a bone.

In another aspect, provided herein is a bone fixation plate, including a first plate portion, a second plate portion, and a third plate portion. The first plate portion including at least one screw hole for receiving at least a first bone screw for attachment to a first bone segment. The second plate portion including at least one slot for receiving at least a second bone screw for attachment to a second bone segment. The third plate portion positioned adjacent to the first plate portion and the second plate portion, the third plate portion configured to guide the cutting of a bone to form the first bone segment and the second bone segment.

In yet another aspect, provided herein is a method of altering a bone, including aligning a bone fixation device on an exposed bone. The bone fixation device including a first portion with at least one first opening, a second portion with at least one second opening, and a third portion positioned between the first portion and the second portion. The third portion including a cutting slot configured to receive a cutting device and a tab portion extending downward relative to a bottom surface of the first portion and the second portion. The method may also include drilling at least one first hole in the exposed bone through the at least one first opening in the bone fixation device and inserting at least one fastener into the at least one first hole to couple the bone fixation device to the exposed bone. The method may further include inserting a cutting device into the cutting slot in the bone fixation device to cut the exposed bone into a first bone segment and a second bone segment. The method may also include reducing the first bone segment and the second bone segment to shorten the exposed bone. In addition, the method may include drilling at least one second hole in the exposed bone through the at least one second opening in the bone fixation device and inserting at least one fastener into the at least one second hole.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

DETAILED DESCRIPTION FOR CARRYING OUT THE INVENTION

The present disclosure described herein provides a system and method for corrective surgery and bone fusion. More specifically, a method and system for shortening of a bone are disclosed. The present disclosure facilitates secure fixation of bone by providing a means for managing any type of bone segment. Conventional fixation plates or external bone fixators are not able to alleviate problems that can occur when a distal bone segment is not aligned with the fixation plate. Embodiments of the present disclosure provide fixation plates including integral cutting surfaces, for example, in the form of built in jig guides that facilitate bone shortening. The terms "fixation plate," "bone fixation device," "fixation device," and "plate" may be used interchangeably herein as they essentially describe the same device.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device nearest the torso, while "distal" indicates the portion of the device farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 25:
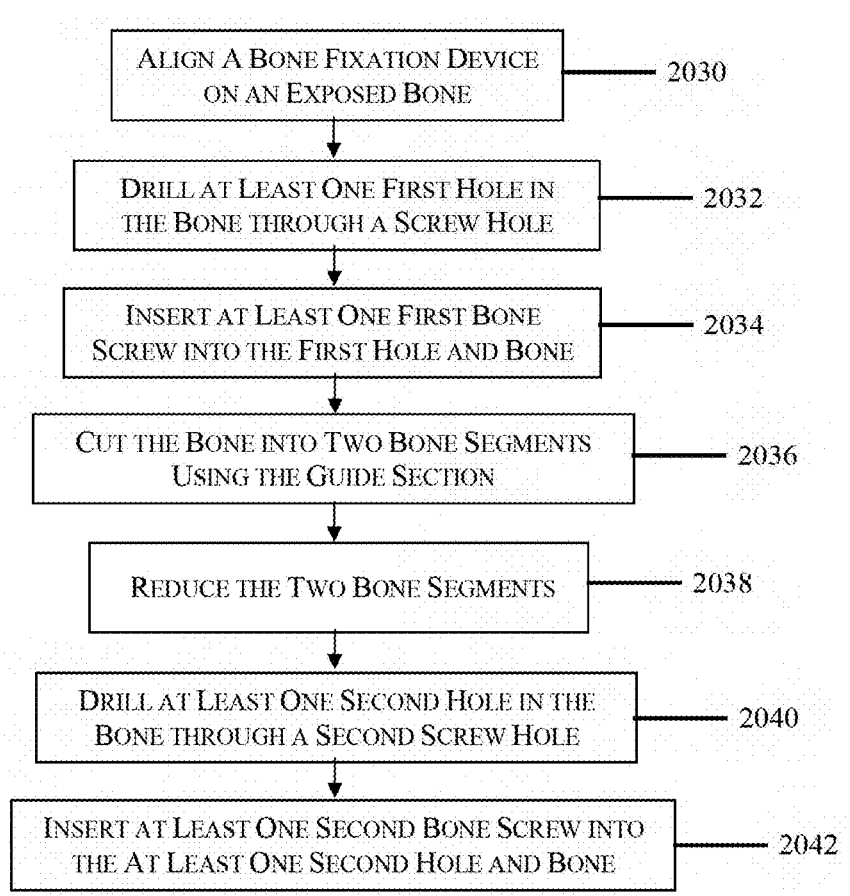
FIG. 25 depicts another embodiment of a surgical method for shortening a bone, in accordance with an aspect of the present invention.

Provided herein is a system and method for carrying out corrective surgery and bone fixation. In the various embodiments described herein and corresponding with the Figures provided herewith, a bone fixation method and system are described with respect to a bone. It is understood by one of ordinary skill in the art that the various embodiments may apply to any type of bone in any type of mammal, including, but not limited to, humans. By way of specific example, in one embodiment as shown in FIG. 25, a plate is positioned over a bone 2030. Holes are drilled into a first segment of the bone through at least one screw hole of the plate on a first portion of the plate 2032. Screws are inserted into the holes on the first portion of the plate to affix the plate to the bone at the first segment of the bone 2034. At least one cut is made into the bone to remove a portion of the bone 2036. The at least one cut is made based on a third portion of the plate which serves as a guide for making cuts into the bone. The cuts into the bone may be made by, for example, a saw, or any other apparatus or device used for cutting bone known to one of ordinary skill in the art. In one embodiment, the cuts may be made, for example, such that a first cut is made at a distal side of the bone with respect to the first portion of the plate attached to the bone, followed by a second cut at a proximal side of the bone closer to the first portion. This facilitates stability in the bone as the cuts are made. Once the at least one cut is made, a portion of the bone may be removed. The second bone segment is then repositioned with respect to the affixed first bone segment 2038. For example, the second bone segment may be moved to a position in closer proximity to the first bone segment. At least one hole may then be drilled through at least one compression slot on a second portion of the plate 2040. The at least one screw may be inserted into the at least one hole through the at least one compression slot on the second portion of the plate 2042. As the at least one screw is tightened, a compressive force may be applied to the second bone segment causing the second bone segment to move towards the first bone segment and form a corrective construct.

Figure 1:
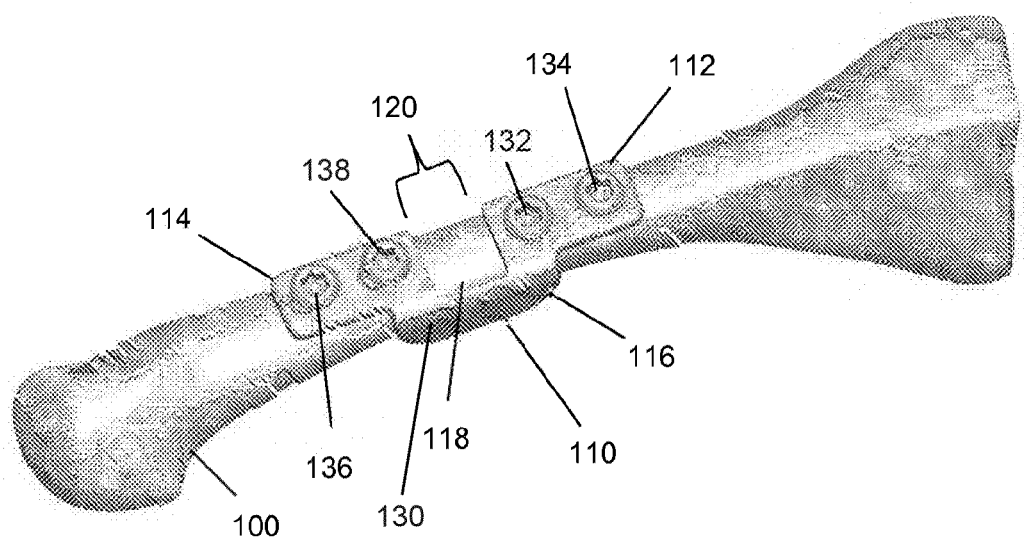
FIG. 1 depicts a perspective view of an embodiment of a bone fixation device, for facilitating a cut of a discrete length, attached to a bone, in accordance with an aspect of the present invention.
Figure 2:
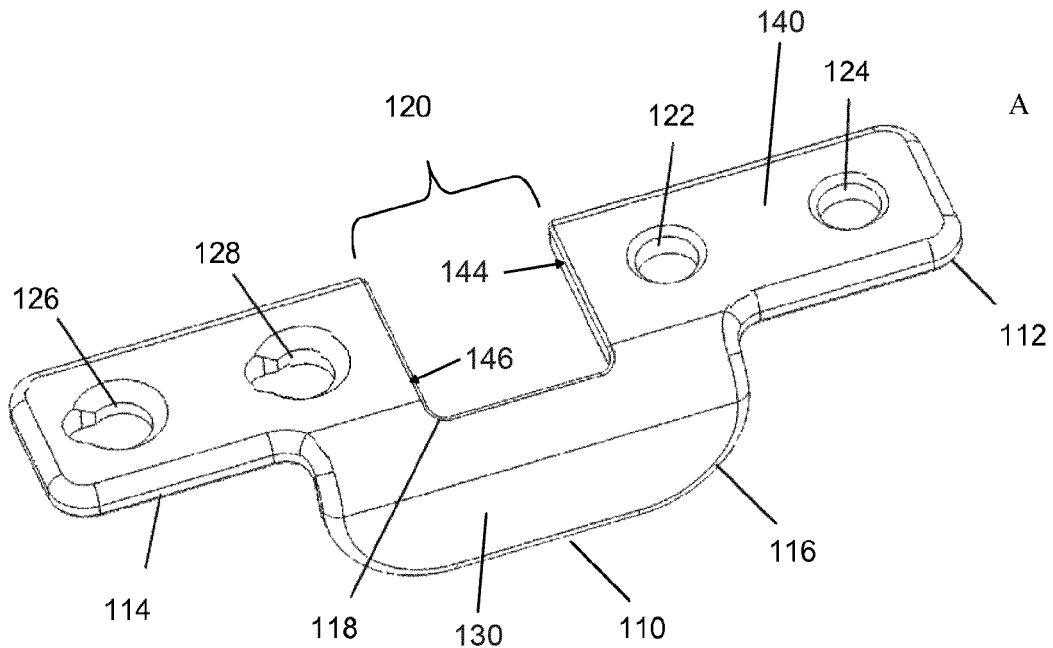
FIG. 2 depicts a top perspective view of the bone fixation device of FIG. 1, in accordance with an aspect of the present invention.
Figure 3:
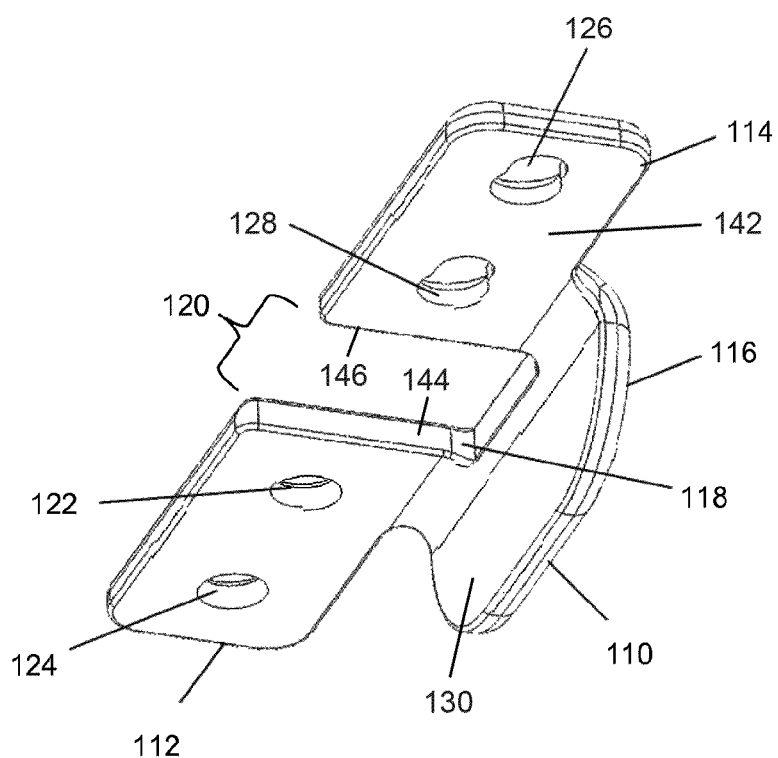
FIG. 3 depicts a bottom perspective view of the bone fixation device of FIG. 1, in accordance with an aspect of the present invention.

FIG. 1 illustrates a perspective view of a bone fixation device or plate 110 attached to a bone. As seen in FIG. 1, the bone 100 has been corrected using a plate 110 and the correction is shortening of the bone. FIGS. 1-3 show the plate 110 which includes a first plate portion 112, a second plate portion 114, and a third plate portion 116. The first plate portion 112 may be, for example, a proximal plate portion on a proximal part of a bone, and the second plate portion 114 may be, for example, a distal plate portion on a distal part of the bone. The third plate portion 116 may be a portion of the plate 110 joining the first plate portion 112 and the second plate portion 114. The third plate portion 116 may further include a guide section 118 that facilitates cutting of the bone prior to shortening of the bone. For example, guide section 118 may include a slot or cut guide 120 of a discrete length to guide a surgeon or medical practitioner in cutting the bone 100 to remove a portion of the bone 100 before repositioning a segment of the bone 100 to form a corrective construct.

The third plate portion 116 may also include a tab 130 which may be relatively perpendicular or angled in some fashion to the first plate portion 112 and the second plate portion 114. The tab 130 may be, for example, planar or curved, as shown in FIG. 3, the tab 130 may be curved relative to the top surface of the third plate portion 116 to correspond to or match the radius of curvature of the bone 100. By way of specific example, the tab 130 may be approximately half the length of the plate 110 and the tab may extend down with a height that corresponds to the width of the plate 110, although other dimensions are also contemplated. The plate 110 may also include a top surface 140 and a bottom surface 142. The tab 130 may extend downward from the bottom surface 142 of the plate 110 and be generally perpendicular to the bottom surface 142 of the plate 110. Alternatively, the tab 130 may be arced relative to the bottom surface 142 as the tab 130 extends downward with the curve or arc corresponding to the shape of the bone 100. The tab 130 may be configured to ensure that when the resected section is moved proper alignment is maintained. Thus, the tab 130 may act as an alignment and/or positioning guide. In addition, the tab 130 may provide stability to the plate 110 and protection to the surrounding tissues when the cutting device is inserted into the cut guide 120. The top surface 140 and bottom surface 142 of the plate 110 may be planar or arcuate and configured to match the shape of the bone surface or convex and may assist with alignment and movement of the bone segment.

As shown in FIGS. 1-3, the slot 120 may include at least two cutting surfaces 144, 146. The at least two cutting surfaces may include a proximal cutting surface 144 and a distal cutting surface 146. By way of specific example, the proximal cutting surface 144 and the distal cutting surface 146 may be primarily perpendicular to the long or longitudinal axis A of the plate 110. In other embodiments, the cutting surfaces 144, 146 may be angled in another direction or plane of the plate 110 to enable a surgeon to make cuts in any direction to correct a bone deformity. The cutting surfaces 144, 146 may be planar or angled. The cutting surfaces 144, 146 may be separated by a width which may be, for example, between approximately 0.5 mm and 15 mm, and more preferably between approximately 0.5 mm and 5 mm. The shape of the slot 120 may be configured to facilitate compression of the two bone segments.

FIGS. 1-3 show the first plate portion 112 including holes 122, 124 extending from the top surface 140 through the bottom surface 142. The holes 122, 124 may be configured for receiving bone screws 132 and 134, for example, to affix the proximal part or first segment of the bone 100 to the plate 110. In addition, the second plate portion 114 may include compression slots 126, 128 extending from the top surface 140 of the plate 110 through the bottom surface 142 of the plate 110. The compression slots 126, 128 may be configured for receiving bone screws 136 and 138, for example, to affix the distal part or second segment of the bone 100 to the plate 110 after a portion of the bone 100 has been removed based on the slot 120 of the guide section 118. Tightening of bone screws 136 and 138 may cause an application of compressive force that results in the second bone segment moving towards the first bone segment to facilitate altering a bone.

In other embodiments, plate 110 may include additional portions for affixing to the bone 100. Additionally, while two bone screws 132, 134, 136, and 138 are shown to attach the bone 100 to each of the first plate portion 112 and the second plate portion 114, it is understood by one skilled in the art that any number of screws may be used, and that the first plate portion 112 and the second plate portion 114 may be adapted to support the screws accordingly. The third plate portion 116 may furthermore take on different configurations, with various shapes, such as, square, rectangle, a portion of a circle, and others, which may correspond to the shape of the bone, to facilitate cuts of different lengths or of different angles into the bone to facilitate removal of a portion of the bone 100.

Figure 4:
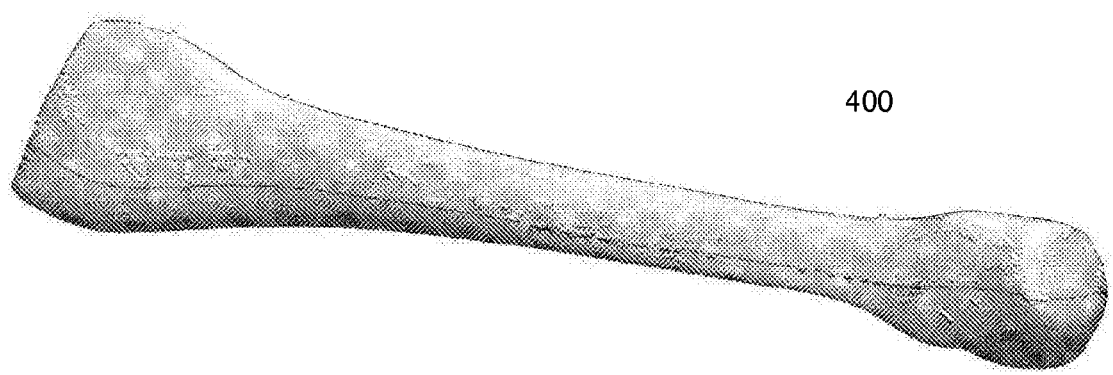
FIG. 4 depicts an exemplary bone, in accordance with an aspect of the present invention.

In accordance with the embodiments described herein, a method for applying a plate to a bone to facilitate bone shortening is disclosed. This method is described with respect to FIGS. 4-13. A bone 400, as shown in FIG. 4, represents any bone of a mammal that can receive a bone fixation device or plate as described herein to facilitate bone shortening after a cut in the bone 400 has been made and/or a portion of the bone 400 is removed.

Figure 5:
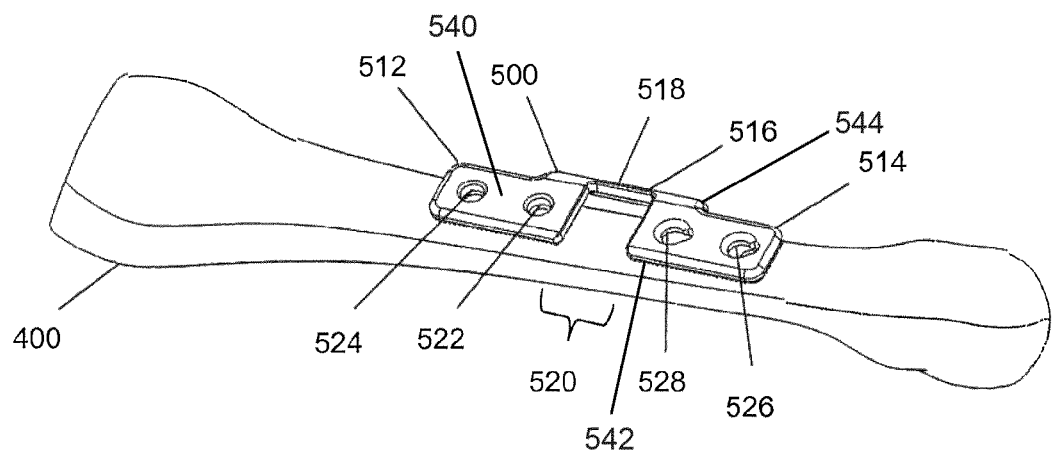
FIG. 5 depicts a top perspective view of the bone of FIG. 4 with the bone fixation device of FIG. 1 placed on the bone, in accordance with an aspect of the present invention.

As shown in FIG. 5, a plate 500 is aligned on top of bone 400 with the bottom surface 542 of the plate 500 contacting the bone 400. In addition, the tab 544 of the third plate portion 516 may be configured to align with a side of the bone 400. The plate 500 may be of the type described above with reference to plate 110, which will not be fully described again here for brevity sake. The plate 500 may be positioned over the bone 400 at any position, but preferably near a position where the bone shortening procedure is to take place, and preferably where a cut or cuts are to be made to bone 400 to remove at least a portion of the bone. The plate 500 includes a first plate portion 512, a second plate portion 514, and a third plate portion 516. The first plate portion 512 may be, for example, a proximal plate portion aligned on a proximal part of a bone, and the second plate portion 514 may be, for example, a distal plate portion aligned on a distal part of the bone. The third plate portion 516 may be a portion of the plate 500 joining the first plate portion 512 and the second plate portion 514 and including a guide section 518 to facilitate cutting of the bone. For example, the guide section 518 may include a slot or cut guide 520 of a discrete length to guide a surgeon or medical practitioner in cutting the bone 400 to remove a portion of the bone 400 before repositioning a segment of the bone 400 to form a corrective construct. Thus, the third plate portion 516 may be aligned over the portion of the bone 400 to be removed.

Figure 6:
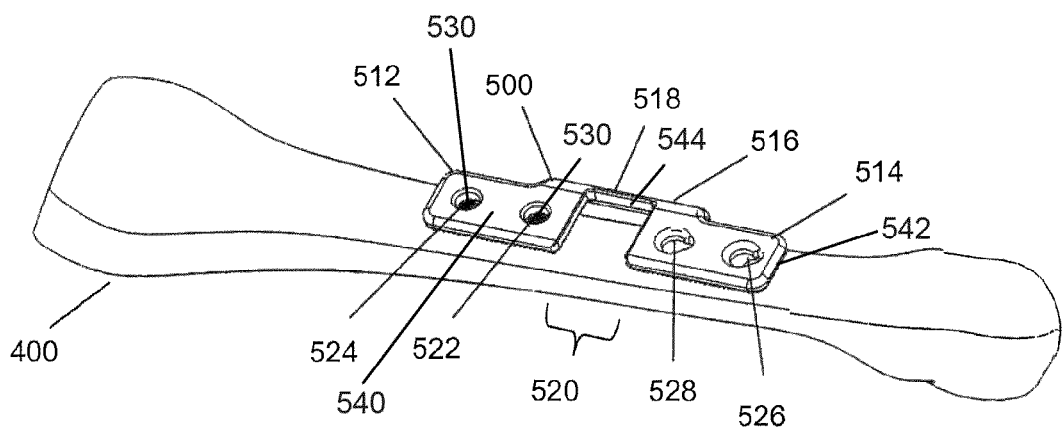
FIG. 6 depicts a top perspective view of the bone fixation device of FIG. 1 and the bone of FIG. 4 after holes are drilled into the bone through two screw holes in the bone fixation device, in accordance with an aspect of the present invention.
Figure 7:
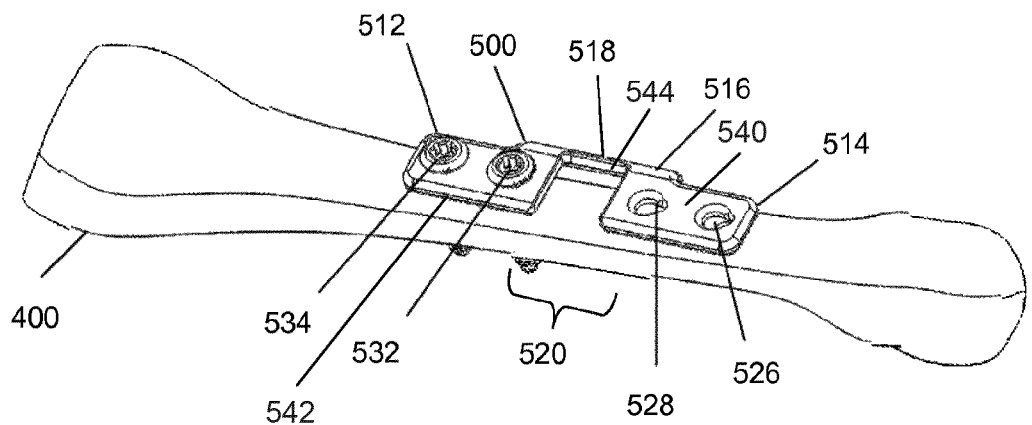
FIG. 7 depicts a top perspective view of the bone fixation device of FIG. 1 and the bone of FIG. 4 after screws are inserted into the two screw holes to affix bone fixation device to the bone, in accordance with an aspect of the present invention.

FIG. 6 illustrates holes 530 drilled into the bone 400. The holes 530 are drilled through screw holes 522 and 524 of first plate portion 512 to receive bone screws 532, 534, as shown in FIG. 7. The bone screws 532, 534 may be used for affixing or attaching the plate 500 to the proximal part or first segment of the bone 400 at a first end.

Figure 8:
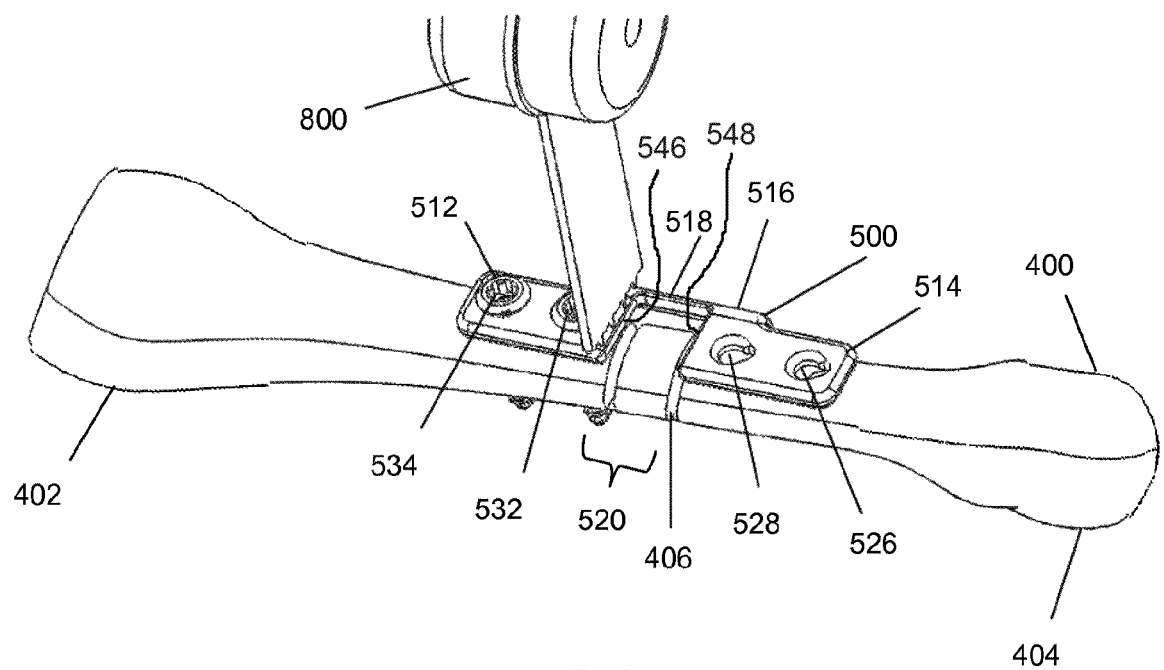
FIG. 8 depicts a top perspective view of the bone fixation device of FIG. 1 and the bone of FIG. 4 showing a portion of the bone being cut using a guide of the bone fixation device, in accordance with an aspect of the present invention.
Figure 9:
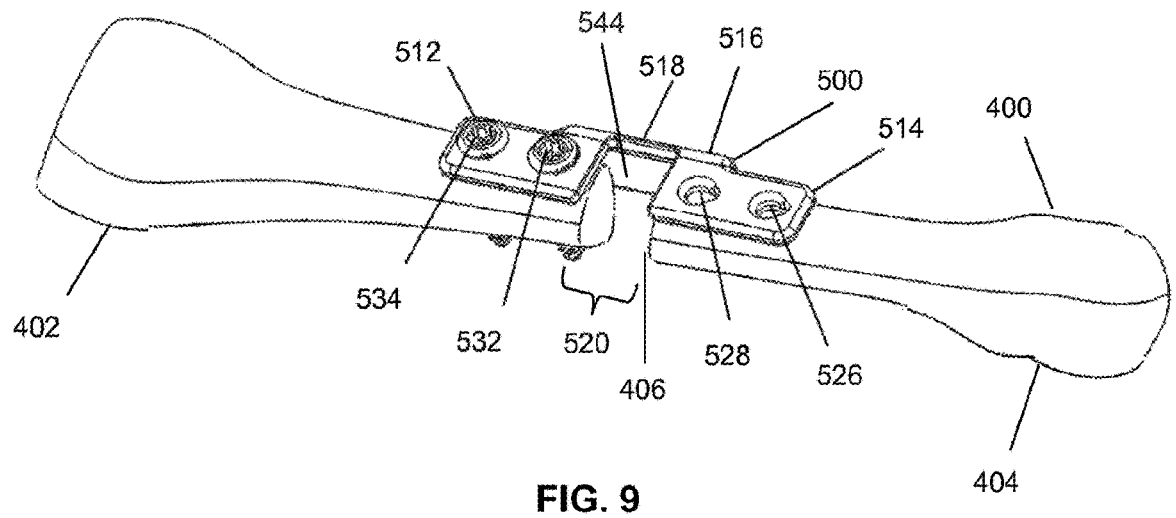
FIG. 9 depicts a top perspective view of the bone fixation device of FIG. 1 and the bone of FIG. 4 after the portion of the cut bone is removed, in accordance with an aspect of the present invention.

As shown in FIG. 8, a cutting device 800, for example, a saw may be used to cut a portion of the bone 400 between the first and second segments using at least one of the proximal cutting surface 546 and the distal cutting surface 548 of the slot 520 of the third plate portion 516. By way of specific example, two cuts may be made in the bone 400 to separate the bone 400 into a first bone portion 402 that is attached to the plate 500 with the bone screws 532 and 534, a second bone portion 404, which may be adjusted for bone angle or length correction, and a third bone portion 406 which is to be removed. A first cut may be made, for example, using the proximal cutting surface 546 as a guide and a second cut may be made using the distal cutting surface 548 as a guide. Alternatively, the second cut could be made, for example, at any position between the proximal cutting surface 546 and the distal cutting surface 548 to enable a surgeon to make a cut smaller than the width of the slot 520. The cuts may be made using, for example, a saw 800. In one embodiment, cuts may be made such that a first cut is made at a distal side of the bone 400 with respect to the first portion 512 of the plate 500, followed by a second cut at a proximal side of the bone 400 closer to the first portion 512. The distal side of the bone 400 may be cut before the proximal side of the bone 400 to facilitate stability. The third bone portion 406 is then removed as shown in FIG. 9, although if the slot 520 corresponds to the size of a blade of the saw 800 there will not be a third bone portion 406 for removal.

Figure 10:
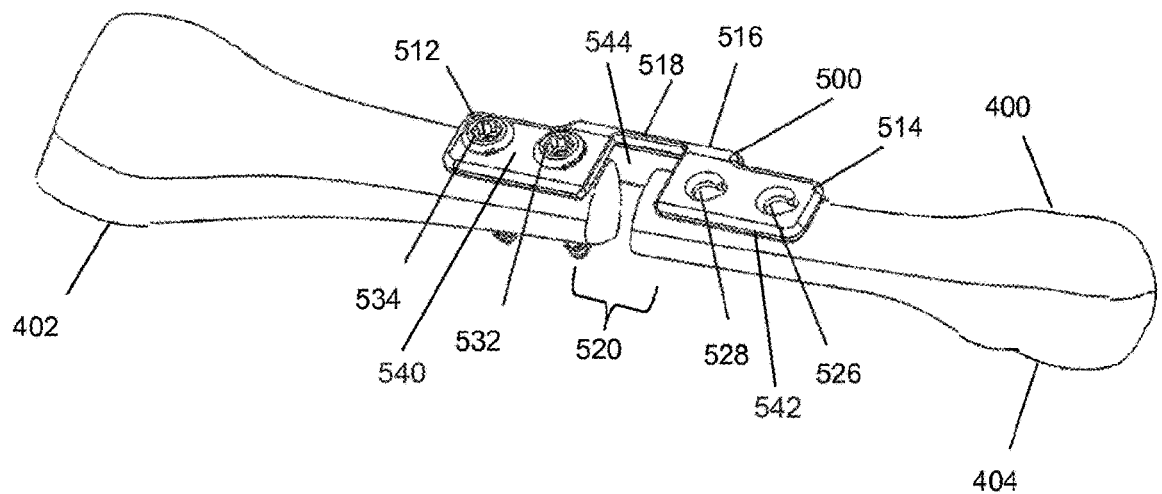
FIG. 10 depicts a top perspective view of the bone fixation device of FIG. 1 and the bone of FIG. 4 during the reduction of the second bone segment of the bone relative to the first bone segment affixed to the bone fixation device, in accordance with an aspect of the present invention.
Figure 11:
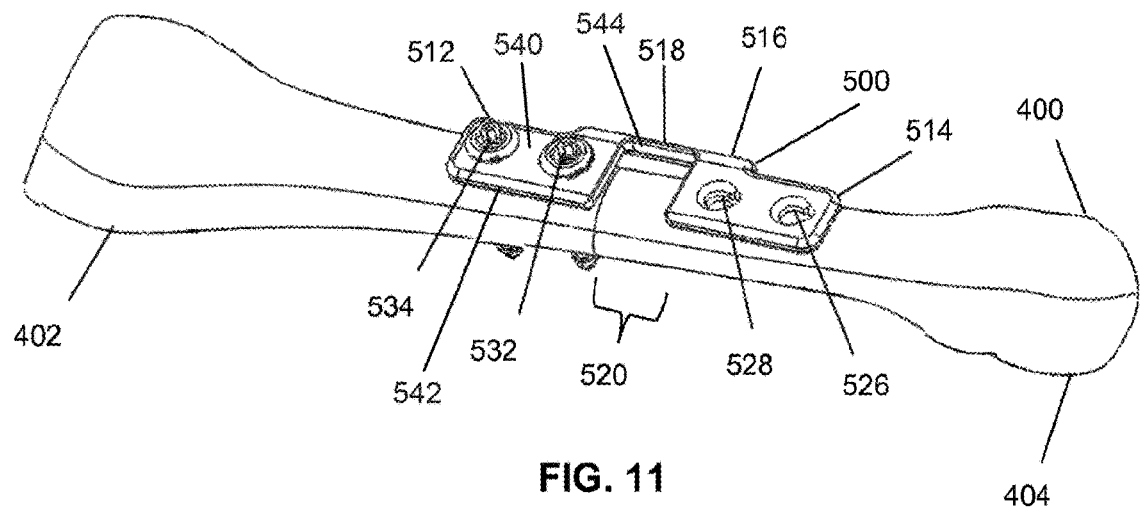
FIG. 11 depicts a top perspective view of the bone fixation device of FIG. 1 and the bone of FIG. 4 after reduction of the second bone segment relative to the first bone segment, in accordance with an aspect of the present invention.

After the third bone portion 406 is removed, the second bone portion 404 may be moved and positioned relative to the first bone portion 402 that is fixed to the plate 500, as shown in FIG. 10. The tab 544 of the guide section 518 of the third plate portion 516 may act to ensure alignment of the second bone portion 404 when it is moved to shorten the bone 400. The second bone portion 404 may be positioned for correction of the bone, for example, by shortening, reducing, rotating, angling, and/or translating the bone 400. The bone 400 may be shortened or reduced by moving the second bone portion 404 closer to the first bone portion 402 along the interior surface of the tab 544 of the guide section 518 prior to affixing the second bone portion 404 to the second plate portion 514. The second bone portion 404, as shown in FIG. 11, may be moved closer to and adjacent to the first bone portion 402 in preparation for affixing the plate 500 to the second bone portion 404 using the second plate portion 514 to facilitate the union or fusion of the two bone segments 402, 404.

Figure 12:
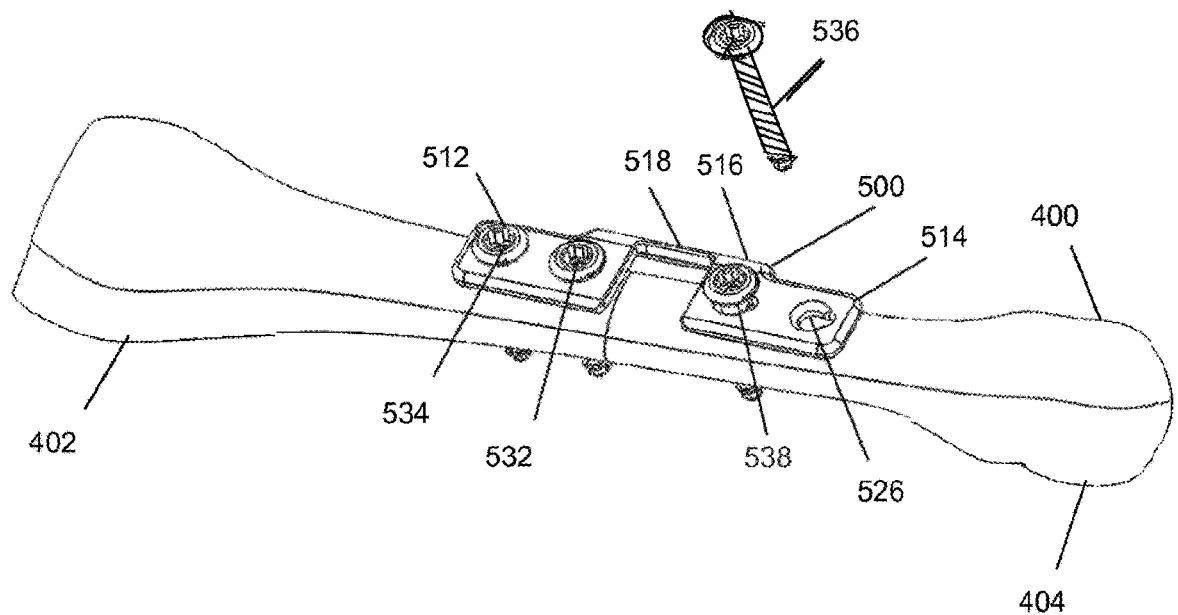
FIG. 12 depicts a top perspective view of the bone fixation device of FIG. 1 and the bone of FIG. 4 during the preparation for the insertion of at least one fastener into the second bone segment, in accordance with an aspect of the present invention.
Figure 13:
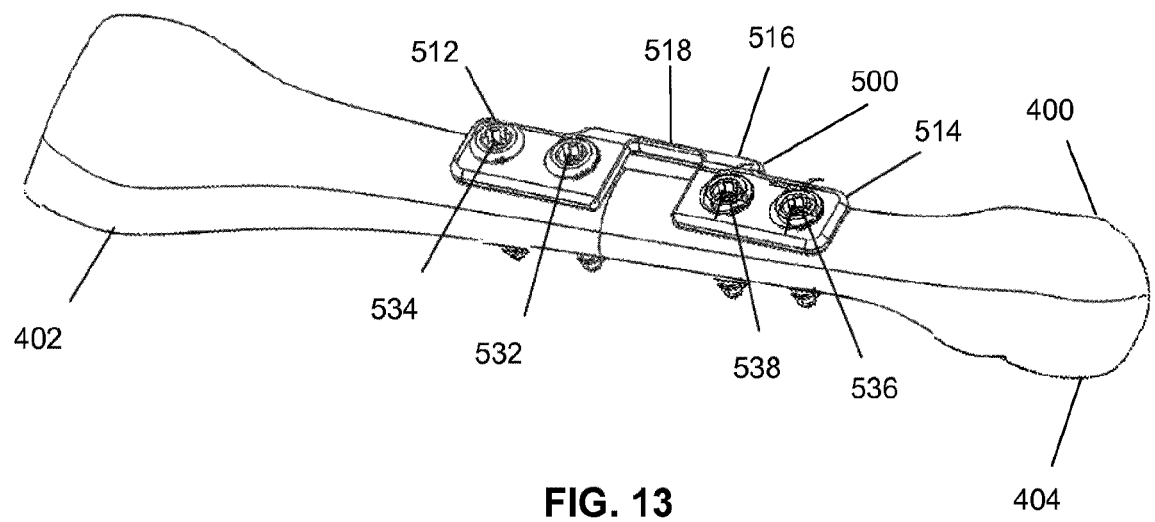
FIG. 13 depicts a top perspective view of the bone fixation device of FIG. 1 and the bone of FIG. 4 after fixation of the bone fixation device to the bone, in accordance with an aspect of the present invention.

Once the bone 400 is shortened or reduced to the desired position, the second plate portion 514 may be secured or affixed to the second bone portion 404. A hole may be drilled through a compression slot 528, 526 and into the bone 400. For example, the hole may be drilled through the compression slot 528 which is closer to the proximal or first bone portion 402. A bone screw 538 may then be inserted into the compression slot 528 and the hole in the bone 400, as shown in FIG. 12. Next a hole may be drilled through the compression slot 526 and a bone screw 536 may be inserted into the compression slot 526 and the hole in the bone 400, as shown in FIG. 13. Alternatively, the holes may be drilled through both compression slots 526 and 528, prior to insertion of a bone screw 538 into the hole through the compression slot 528 and then a bone screw 536 may be inserted into the hole through the compression slot 526. The holes may be drilled using a drill. The compression slots 526, 528 are configured to assist with bone fusion.

As shown by FIG. 13, both bone screws 536 and 538 have been inserted into the compression slots 526, 528 of second plate portion 514 to affix plate 500 to the distal part or second segment of the second bone portion 404. Tightening or screwing of bone screws 536 and 538 into the compression slots 526, 528 of second plate portion 514 may cause an application of compressive force resulting in the second bone portion 404 moving towards the first bone portion 402 to complete the shortening process and facilitate bone fusion. The result is a corrective construct of bone 400 with attached plate 500.

Figure 14:
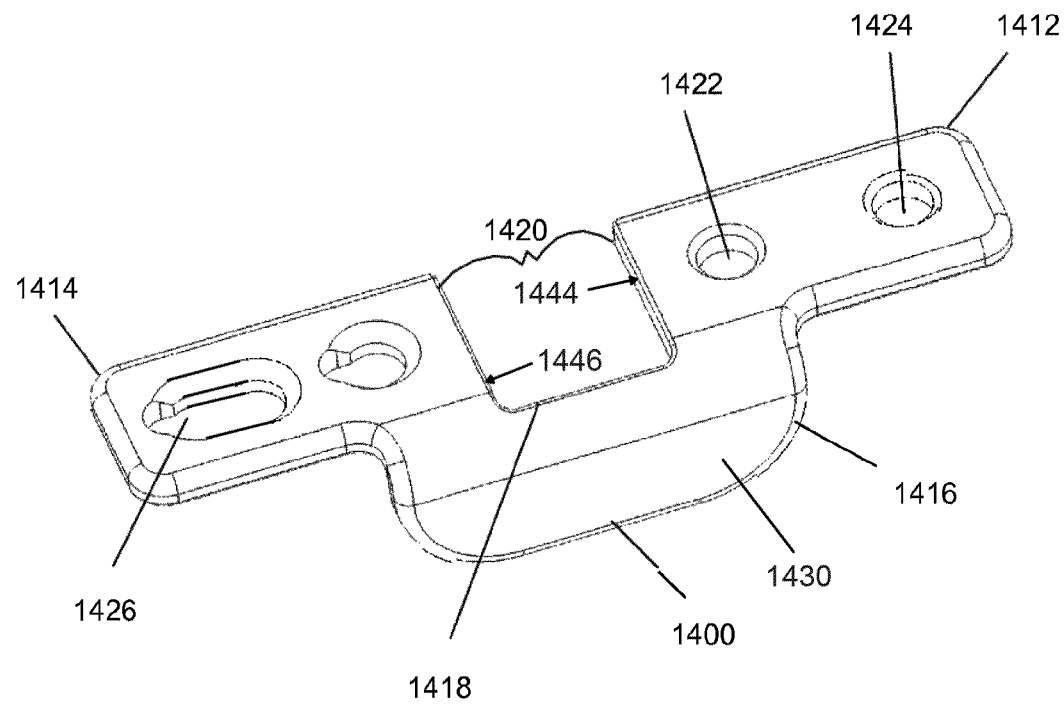
FIG. 14 depicts a top perspective view of another embodiment of a bone fixation device with a full compression slot, in accordance with an aspect of the present invention.

FIG. 14 illustrates an exemplary plate 1400 with a full compression slot 1424. The plate 1400 may be similar to the plates 110 and 500 as discussed above in greater detail and for brevity sake the plate 1400 will not be discussed completely here. The plate 1400 may include a first plate portion 1412, a second plate portion 1414, and a third plate portion 1416. The first plate portion 1412 may be, for example, a proximal plate portion on a proximal part of a bone, and the second plate portion 1414 may be, for example, a distal plate portion on a distal part of the bone. The third plate portion 1416 may be a portion of the plate joining the first plate portion 1412 and the second plate portion 1414 and may act as an alignment and positioning guide. The third plate portion 1416 may also include a guide section 1418 that facilitates cutting of the bone for a bone shortening procedure. For example, the guide section 1418 may include a slot or cut guide 1420 of a discrete length to guide a surgeon or medical practitioner in cutting the bone to remove a portion of the bone before repositioning a segment of the bone to form a corrective construct. The slot 1420 may include a proximal cutting surface 1444 and a distal cutting surface 1446. The proximal and distal cutting surfaces 1444, 1446 may be generally perpendicular and can be straight or angled relative to the longitudinal axis of the plate 1400. In addition, the proximal and distal cutting surfaces 1444, 1446 provide flat cutting surfaces for the cutting device. By way of specific example, a surgeon may use both the cutting surfaces 1444, 1446 to remove a portion of bone, although it is also contemplated that a surgeon may use one of the cutting surfaces 1444, 1446 and then make a second cut at a position between the two cutting surfaces 1444, 1446 without a guide. The third plate portion 1416 may also include a tab 1430 which may be relatively perpendicular to the first plate portion 1412 and the second plate portion 1414. The tab 1430 may be, for example, planar or curved, as shown in FIG. 3, to correspond to the shape of the bone. The tab 1430 may be configured to engage a side of the bone to facilitate alignment and translation of the bone when resected.

As shown in FIG. 14, the first plate portion 1412 may include screw holes 1422 and 1424 for receiving bone screws (not shown), for example, to affix the proximal part or first segment of the bone to the plate 1400. The second plate portion 1414 may include a compression slot 1426 for receiving a bone screw (not shown) to affix the distal part or second segment of the bone to the plate 1400 after a portion of the bone has been removed based on the cut guide 1420 of the guide section 1418. Tightening of a bone screw within compression slot 1426 causes an application of compressive force that results in the second bone segment moving towards the first bone segment to form a corrective construct including shortening of the length of the bone. The plate 1400 functions similarly to plates 110 and 500 described above. However, a full or elongated compression slot 1426 facilitates a greater range of compression in bringing together a second portion of the bone with a first portion of the bone. The elongated compression slot 1426 may be positioned anywhere along the second plate portion 1414 to correspond to the correction necessary for a specific bone correction.

Figure 15:
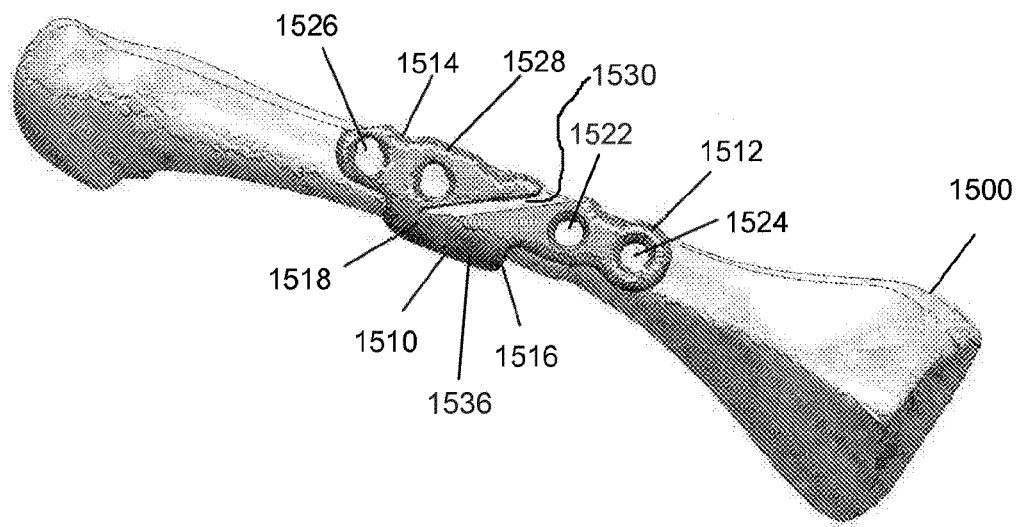
FIG. 15 depicts a top perspective view of another bone fixation device embodiment with an angled cutting guide on a bone, in accordance with an aspect of the present invention.
Figure 16:
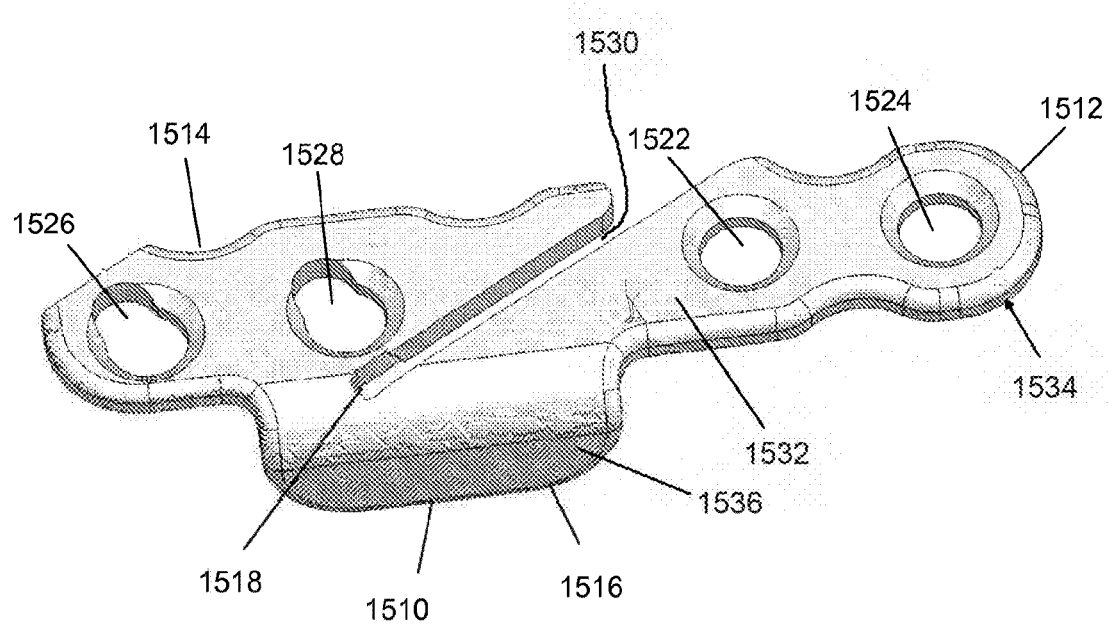
FIG. 16 depicts a top perspective view of the bone fixation device of FIG. 15, in accordance with an aspect of the present invention.

FIGS. 15 and 16 show another embodiment of plate 1510 with an angled cut placed on a bone 1500. The plate 1510 is configured for facilitating an angled cut in the bone 1500 for a bone shortening procedure. The angled cut may provide increased surface area for fusion of the bone segments. The plate 1510 may include a first plate portion 1512, a second plate portion 1514, and a third plate portion 1516. The first plate portion 1512 may represent, for example, a proximal plate portion on a proximal part of the bone 1500, and the second plate portion 1514 may represent, for example, a distal plate portion on a distal part of the bone 1500. The third plate portion 1516 represents a portion of the plate 1510 joining the first plate portion 1512 and the second plate portion 1514. The third plate portion 1516 may further include a guide section 1518 that facilitates cutting of the bone prior to shortening of the bone. For example, guide section 1518 may include a cut guide or oblique angle cutting slot 1530 to guide a surgeon or medical practitioner in cutting the bone 1500 before repositioning a segment of the bone 1500 to form a corrective construct. The third plate portion 1516 may also include a tab portion 1536 which may extend away from the plate 1510 in a downward direction relative to the bottom surface of the plate 1510 in a relatively perpendicular, angled or arced fashion from the first plate portion 1512 and the second plate portion 1514. The tab portion 1536 may be, for example, planar or curved, as shown in FIGS. 15-16, to correspond to the shape of a side of the bone 1500. The tab portion 1536 may also be configured to provide support along the length of the plate 1510 corresponding to at least the location of the cutting slot 1530.

The plate 1510 may also include a top surface 1532 and a bottom surface 1534, as shown in FIG. 16. The first plate portion 1512 may include at least one screw hole 1522, 1524 extending from the top surface 1532 through the plate 1510 to the bottom surface 1534. The at least one screw hole 1522, 1524 may be configured for receiving at least one bone screw (not shown), for example, to affix the proximal part or first segment of the bone 1500 to the plate 1510. The second plate portion 1514 may include at least one compression slot 1526, 1528 extending from the top surface 1532 of the plate 1510 through to the bottom surface of the plate 1534. The at least one compression slot 1526, 1528 may be configured for receiving at least one bone screw (not shown) to affix the distal part or second segment of the bone 1500 to the plate 1510 after a portion of the bone 1500 has been removed using the cutting slot 1530 of the guide section 1518. Tightening of bone screws within the at least one compression slot 1526, 1528 cause application of compressive force that results in the second bone segment moving towards the first bone segment to form a corrective construct and facilitate fusion. The cut guide or oblique angle cutting slot 1530 allows for an angled cut to be made to bone 1500. The cutting slot 1530 may have a width of, for example, approximately 0.5 mm to 5 mm, and an angle of, for example, approximately 5 to 90 degrees from the longitudinal axis of the plate 1510. The cutting slot 1530 may, for example, have a width corresponding to the thickness of the saw selected for cutting the bone to enable the surgeon to cut the bone into two segments with a single cut. Alternatively, as described in greater detail above, the cutting slot 1530 may, for example, have a width that requires the surgeon to make two cuts in order to remove a portion of the bone.

Figure 17:
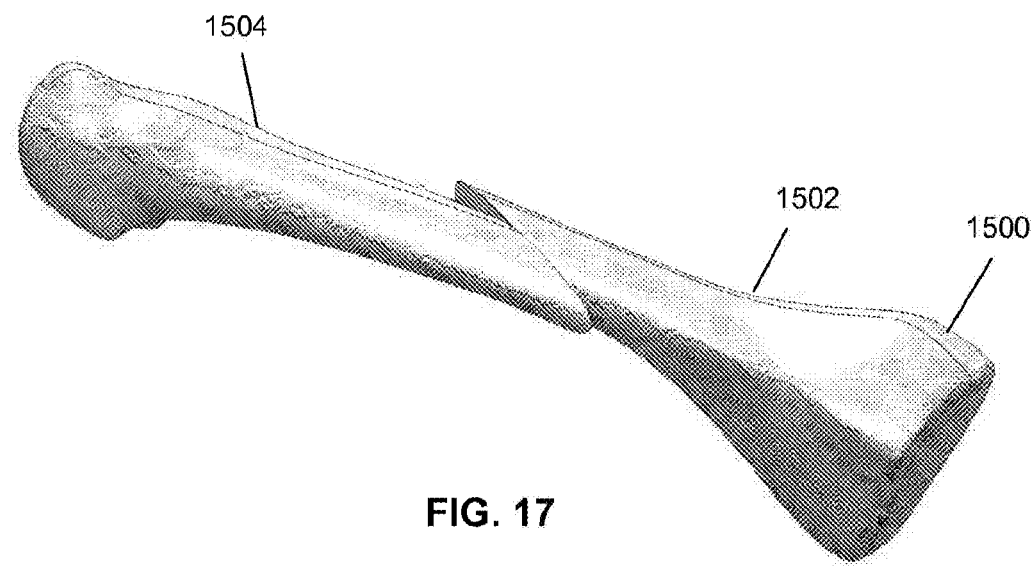
FIG. 17 depicts a top perspective view of the bone of FIG. 15 after a portion of the bone is removed and reduction of the bone is performed, in accordance with an aspect of the present invention.

FIG. 17 shows the bone 1500 after the plate 1510 has been used to cut the bone into at least two segments. The bone 1500 is cut to divide the bone 1500 into a first bone portion 1502 and a second bone portion 1504 to enable shortening of the bone or correct an angular deformity.

Figure 18:
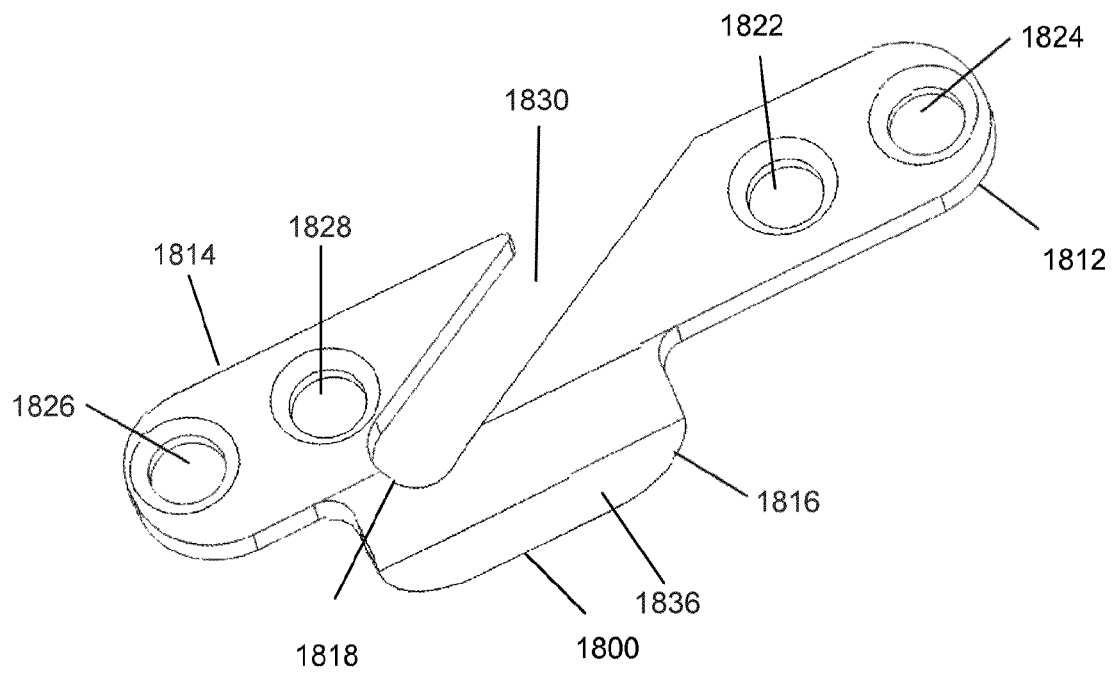
FIG. 18 depicts a top perspective view of another embodiment of a bone fixation device with an oblique cutting guide, in accordance with an aspect of the present invention.
Figure 19:
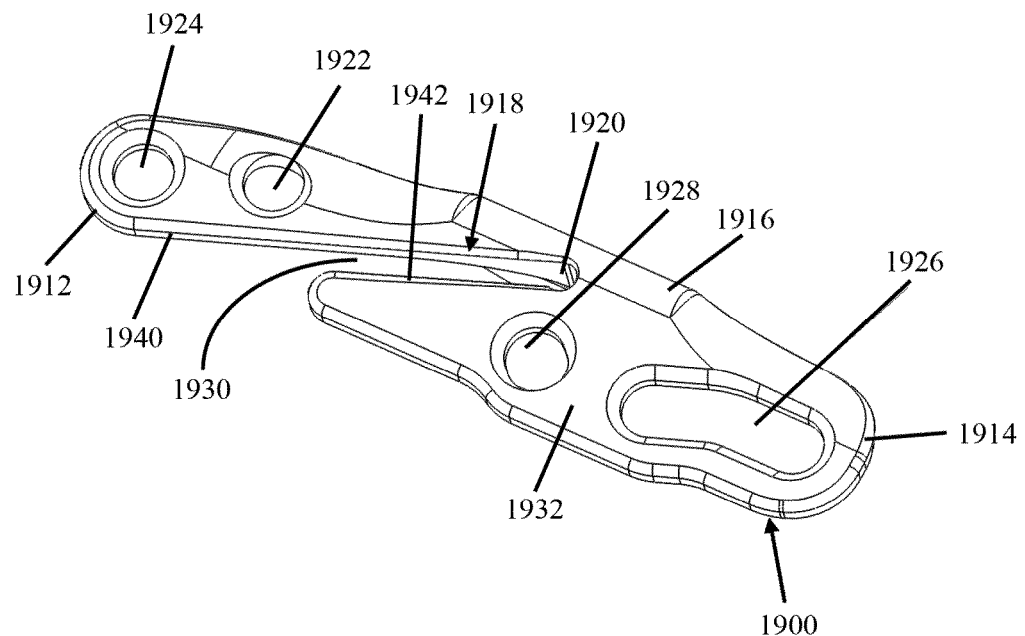
FIG. 19 is a top perspective view of yet another embodiment of a bone fixation device with an angled cutting guide, in accordance with an aspect of the present invention.
Figure 20:
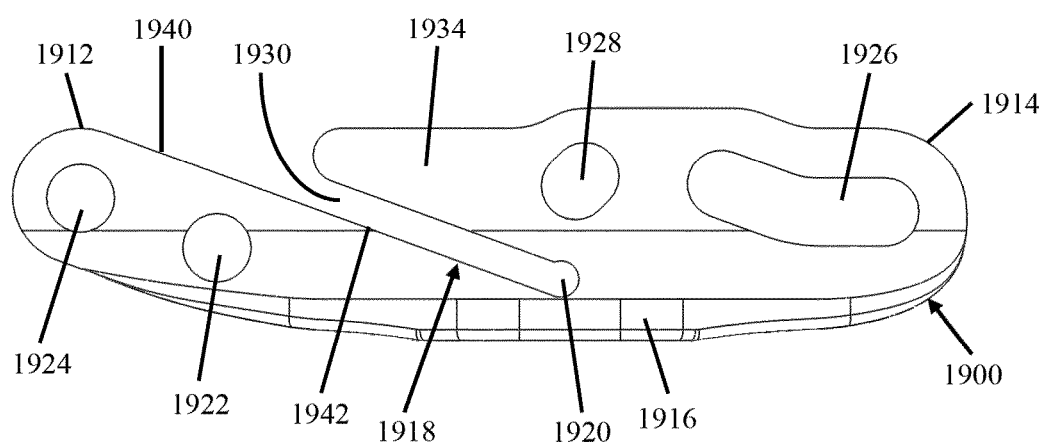
FIG. 20 is a bottom view of the bone fixation device of FIG. 19, in accordance with an aspect of the present invention.

FIG. 18 shows another embodiment of a plate 1800. The plate 1800 is of the type described above with reference to plate 1510, which will not be described again here for brevity sake. The plate 1800 includes a wider oblique cut guide than the plate 1510. The plate 1800 is configured for facilitating removal of a side cut oblique section of a bone for bone shortening or angular correction. The third plate portion 1816 includes the guide section 1818 that facilitates cutting of the bone and includes, for example, a cut guide or wide oblique cutting portion or slot 1830 to guide a surgeon or medical practitioner in cutting the bone before repositioning a segment of the bone to form a corrective construct. The guide section 1818 may also include a tab portion 1836 providing support to the third plate portion 1816 along the cutting portion 1830 of the plate 1800. The wide cut oblique slot 1830 allows for cutting into the bone to remove an oblique portion of the bone. The cutting slot 1830 may have a width of, for example, approximately 0.5 mm to 15 mm, and more preferably approximately 0.5 mm to 5 mm, and an angle of, for example, approximately 5 to 90 degrees from the longitudinal axis of the plate 1800.

Figure 21:
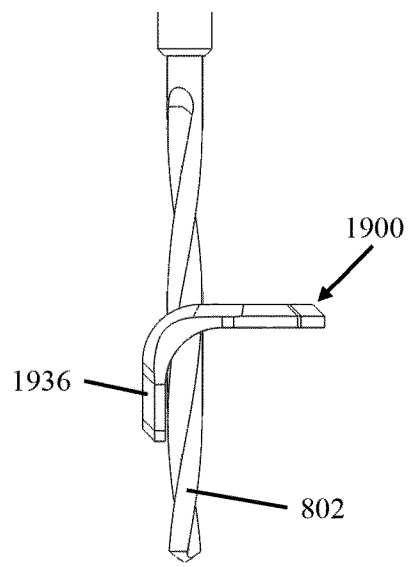
FIG. 21 is an end view of the bone fixation device of FIG. 19 with a drill inserted through an opening in the device, in accordance with an aspect of the present invention.
Figure 22:
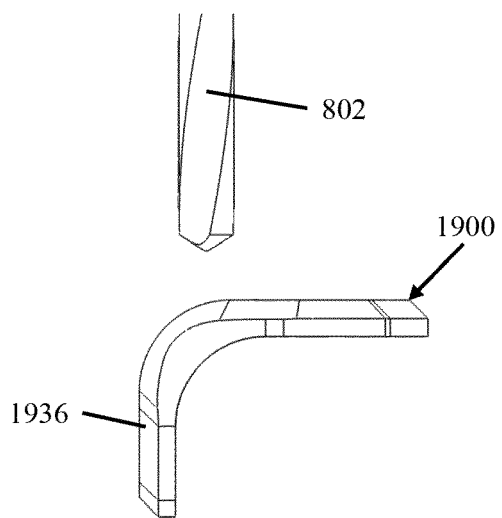
FIG. 22 is an end view of the bone fixation device of FIG. 19 after the drill is removed, in accordance with an aspect of the present invention.
Figure 23:
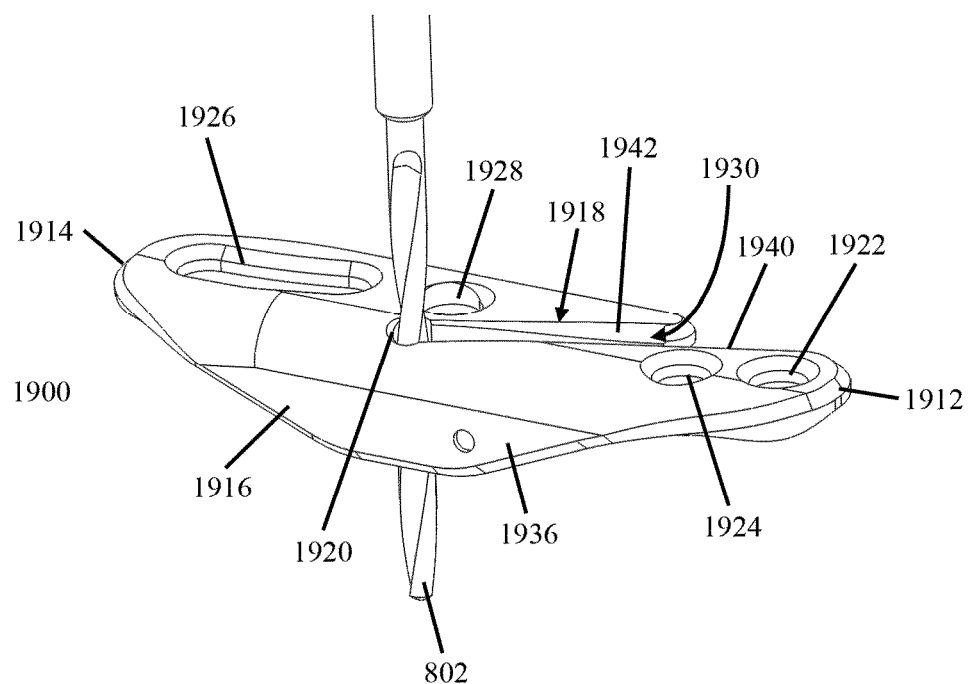
FIG. 23 is a side perspective view of the bone fixation device of FIG. 19 with the drill inserted into an opening in the bone fixation device, in accordance with an aspect of the present invention.

FIGS. 19-23 show another embodiment plate 1900 with a modified outer profile to facilitate placement on the bone. The plate 1900 may be curved or arced along a longitudinal axis, which may assist in aligning the plate 1900 on a bone (not shown) for facilitating an angled cut in the bone. The plate 1900 may include a first plate portion 1912, a second plate portion 1914, and a third plate portion 1916. The first plate portion 1912 may be, for example, a first or proximal plate portion that may be placed on a proximal portion of a bone. While the second plate portion 1914 may be, for example, a second or distal plate portion that may be placed on a distal portion of a bone. The third plate portion 1916 may be a portion of the plate 1900 joining the first plate portion 1912 and the second plate portion 1914 and including an extension member or tab portion 1936. The tab portion 1936 may be, for example, planar or curved, as shown in FIGS. 21-23, to align with a side of a bone. The tab portion 1936 may also be configured to provide additional support along the length of the plate 1900 corresponding to at least the location of the cutting slot 1930.

The third plate portion 1916 may also include a guide section 1918 that may facilitate cutting of the bone prior to shortening of the bone. The guide section 1918 may include, for example, a cut guide or oblique angle cutting slot 1930 to provide a guide for a surgeon or medical practitioner to cut the bone before repositioning a segment of the bone to form a corrective construct. The cutting slot 1930 may include a proximal cutting surface 1940 and a distal cutting surface 1942. The proximal and distal cutting surfaces 1940, 1942 may be generally parallel to each other. The guide section 1918 may also include an apex opening 1920 at the end of the cutting slit 1930 to enable insertion of a drill 802. The apex opening 1920 may allow for the saw to stop prior to contacting the end of the plate 1900 in the guide section 1918 to avoid nicks or other damage to the end of the plate 1900 in the guide section 1918. The opening 1920 may also allow the drill 802 to cut the edge fibers of the bone and periosteum to enable the saw to stop prior to finishing the cut or contacting the tab 1936. The oblique angle cutting slot 1930 allows for an angled cut to be made to the bone. The cutting slot 1930 may have an angle of, for example, approximately 5 to 90 degrees from the longitudinal axis of the plate 1900 and a width of, for example, approximately 0.5 mm to 10 mm and more preferably approximately 0.5 mm to 5 mm.

The first plate portion 1912 and second plate portion 1914 may also include a top surface 1932 and a bottom surface 1934. The first plate portion 1912 may include at least one screw hole, in the depicted embodiment there are two screw holes 1922 and 1924 for receiving bone screws (not shown). The screw holes 1922 and 1924 may extend from the top surface 1932 through the bottom surface 1934 and may be used, for example, to affix the proximal part or first segment of the bone to the plate 1900. The second plate portion 1914 may include at least one compression slot or elongated compression slot 1926 extending from the top surface 1934 through the bottom surface 1934. The at least one compression slot 1926 may extend, for example, from a first end of the second plate portion 1914 toward the first plate portion 1912 and may extend generally along the longitudinal axis of the plate 1900. The compression slot 1926 may be curved as it gets closer to the middle aspect of the plate 1900. The at least one compression screw hole 1928 may be configured for receiving bone screws (not shown). The compression slot 1926 may enable insertion of a bone screw into a distal portion of the bone to enable realignment or compression of the distal portion of the bone with the proximal portion of the bone after a portion of the bone is removed using the guide section 1918. The compression slot 1926 allows the bone screw to slide along the compression slot 1926 to move the distal bone portion to a desired position relative to the proximal bone portion to form a corrective construct. The compression screw hole 1928 provides a space for insertion of a bone screw once the selected alignment is achieved of the distal bone portion with the proximal bone portion to secure the distal bone portion in place.

Figure 24:
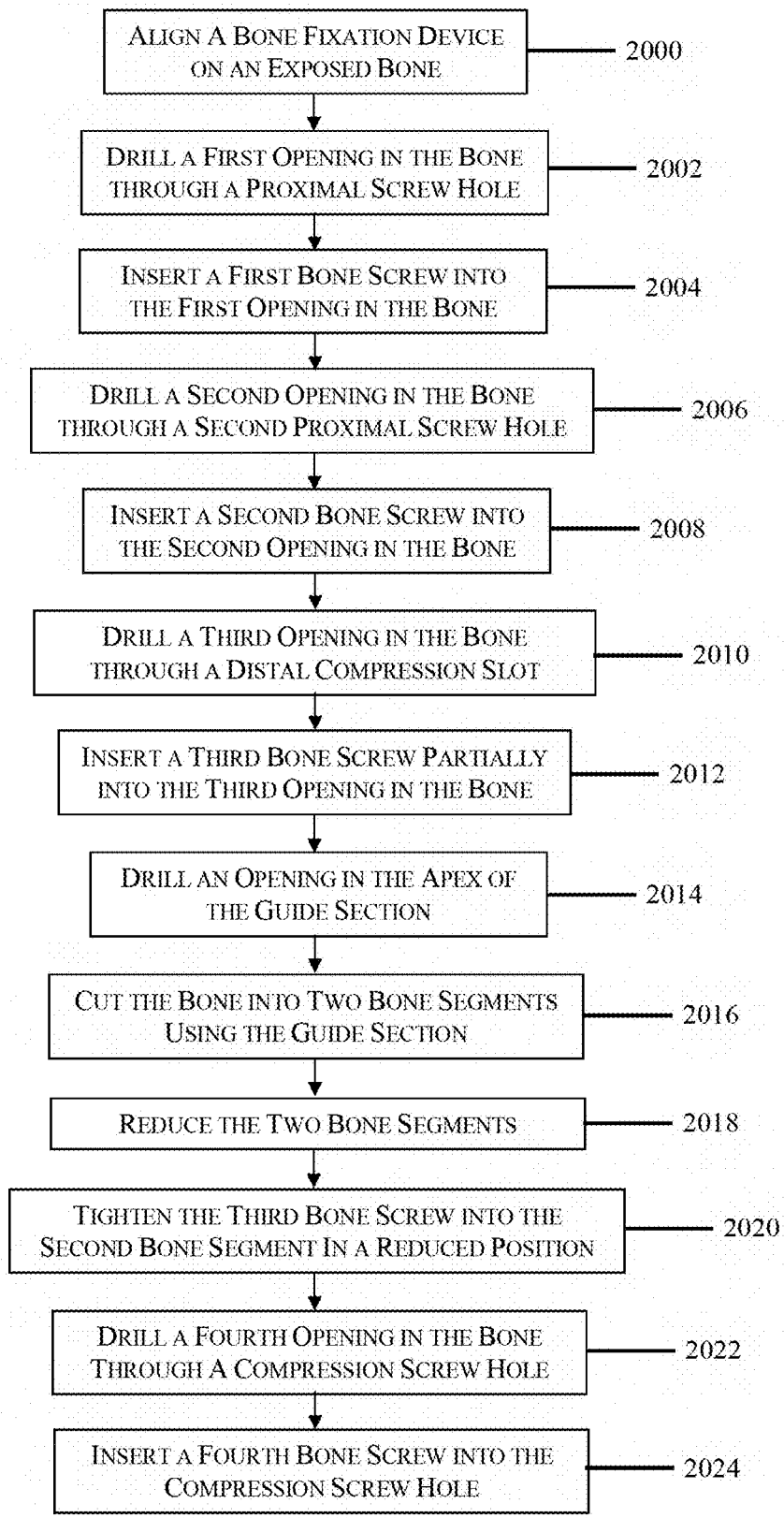
FIG. 24 depicts one embodiment of a surgical method for shortening a bone, in accordance with an aspect of the present invention.

With continued reference to FIGS. 19-23, a method of bone fixation is shown in FIG. 24. The method may include exposing a bone and aligning a bone fixation device on the exposed bone 2000. The bone fixation device may be aligned at any position along the bone and the position for the cut may be selected in an area of the bone which has a greater blood supply to improve healing. An opening may then be drilled into at least one of the screw holes. If the plate 1900 of FIGS. 19-23 is used, a first opening may be drilled into the bone through a proximal screw hole 2002 and a first bone screw may then be inserted into the first opening in the bone 2004. Next a second opening may be drilled into the bone through a second proximal screw hole 2006 and a second bone screw may be inserted into the second opening in the bone 2008. After the bone fixation device is secured at a first end, for example, the proximal end in the depicted embodiment, a third opening may be drilled into the bone through a distal compression slot 2010. Then a third bone screw may be inserted into the bone through the third opening 2012. An opening may then be drilled into the apex opening of the guiding section 2014 and the bone cut into two bone segments using the guide section 2016. The two bone segments may then be reduced 2018 and the third bone screw tightened into the distal bone segment in the reduced position 2020. A fourth opening may then be drilled into the bone through a compression screw hole 2022 and a fourth bone screw inserted into the compression screw hole 2024.

In one embodiment, the bone fixation device 1900 includes a first portion 1912 with at least one first opening 1922, 1924, a second portion 1914 with at least one second opening 1926, 1928, and a third portion 1916 positioned between the first portion 1912 and the second portion 1914, the third portion 1916 configured to guide the cutting of the bone. The third portion 1916 may include a cutting slot 1930 configured to receive a cutting device, and a tab portion 1936 extending downward from a bottom surface of the first portion 1912 and the second portion 1914. The tab portion 1936 relatively perpendicular, angled, or arcuate the top surface of the bone fixation device 1900. The cutting slot 1930 may include a first cutting surface 1940 and a parallel second cutting surface 1942. The first and second cutting surfaces 1940, 1942 may be primarily perpendicular to a long axis of the bone fixation device 1900. The first and second cutting surfaces 1940, 1942 may also be angled relative to the long axis and separated by a width which ranges between 0.5 mm and 10 mm. The cutting slot 1930 may also be angled between 5 degrees and 90 degrees from a longitudinal axis of the bone fixation device 1900. The cutting surfaces 1940, 1942 may also be angled relative to the top and bottom surfaces of the plate 1900. An aperture may be positioned between the first and second cutting surfaces 1940, 1942. The tab portion 1936 may extend downward from a first side of the device 1900 and the aperture of the cutting slot 1930 may extend along a portion of the second side of the device 1900. The cutting slot 1930 may also include an opening 1920 medial a top surface of the third portion 1916 and the first and second cutting surfaces 1940, 1942 may engage the opening 1920 near the tab portion 1936. Further, the first portion 1912 may be arced relative to the second portion 1914. The bone fixation device 1900 may be made of titanium, titanium alloy, stainless steel, cobalt chrome, poly lactic acid, poly ether ether ketone, or carbon fiber composite. The bone fixation device 1900 may also include an angled opening extending from the top surface through the bottom surface of the plate and the angled opening may be angled relative to the top surface of the plate 1900.

In another embodiment a method of altering a bone, includes aligning a bone fixation device on an exposed bone 2000. The bone fixation device including a first portion with at least one first opening, a second portion with at least one second opening, and a third portion positioned between the first portion and the second portion. The third portion configured to guide the cutting of the bone. The method may also include drilling at least one first hole in the exposed bone through the at least one first opening in the bone fixation device 2002 and inserting at least one fastener into the at least one first hole to couple the bone fixation device to the exposed bone 2004. The method may further include drilling at least one second hole in the exposed bone through the at least one second opening in the bone fixation device 2010 and inserting at least one fastener into the at least one second hole to slidingly couple the exposed bone to the bone fixation device 2012. The method may also include inserting a cutting device into a cutting guide in the bone fixation device to cut the exposed bone into a first bone segment and a second bone segment 2016. In addition, the method may include reducing the first bone segment and second bone segment to shorten the exposed bone 2018 and tightening the at least one fastener in the at least one second hole 2020.

The bone fixation devices 110, 500, 1400, 1510, 1800, and 1900 may be made of, for example, titanium, titanium alloy, stainless steel, cobalt chrome, poly lactic acid, poly ether ether ketone, or carbon fiber composite, or any other known metal, metal alloy, polymer, or composite material for forming bone fixation devices. The bone fixation devices 110, 500, 1400, 1510, 1800, and 1900 may also include an angled opening from a top surface through the device to a bottom surface. The angled opening may be configured for insertion of a first crossing bone screw at an angle through a first bone segment and into a second bone segment. The first crossing bone screw may be inserted at an angle into the first and second bone segments to apply direct compressive force to the bone segments. A second crossing bone screw may also be inserted into the side of the first and second bone segments to apply an additional compressive force to the bone segments. In alternative embodiments, either or both of the first and second crossing bone screws may be used to assist with compression of the first and second bone segments to aid in fusion of the bone segments.

Any of the embodiments described herein are not meant to be limiting and any combination of features of the embodiments described herein that could or would be implemented by one of ordinary skill in the art should be recognized.

The foregoing Detailed Description is understood as being in every respect illustrative and exemplary, but not restrictive, and the scope of the embodiments disclosed herein is not to be determined from the Detailed Description, but rather from the claims as interpreted according to the full breadth permitted by the patent laws. It is understood that the embodiments shown and described herein are only illustrative of the principles of the present invention and that various modifications may be implemented by those skilled in the art without departing from the scope and spirit of the disclosure. Those skilled in the art could implement various other feature combinations without departing from the scope and spirit of the disclosure.

Having thus described the preferred embodiments, the invention is now claimed to be:

1. A bone fixation device, comprising:
   a first portion comprising a first surface having a first hole therethrough, a first longitudinal side, a second longitudinal side, and a first interior end closest to a second portion, the first longitudinal side and the second longitudinal side aligned relative to a first longitudinal dimension of the first portion, the first surface bounded by the first longitudinal side, the second longitudinal side, and the first interior end;
   the second portion comprising a second surface having a second hole therethrough, a third longitudinal side, a fourth longitudinal side, and a second interior end closest to the first portion, the third longitudinal side and the fourth longitudinal side aligned relative to a second longitudinal dimension of the second portion, the second surface bounded by the third longitudinal side, the fourth longitudinal side, and the second interior end;
   a third portion positioned between the first portion and the second portion, the third portion configured to guide the cutting of a bone;
   the third portion comprising a cutting slot configured to receive a cutting device, the cutting slot bounded only by the first interior end, the second interior end and a third portion connecting portion connecting said first portion and said second portion; and
   the slot comprising a gap between the first portion and the second portion, the gap opposite said connecting portion and providing communication between the slot and an exterior of the slot to allow access to the slot through the gap;
   the first surface and the second surface separated by the slot;
   wherein the third portion connecting portion comprises a tab portion extending downwardly from said first surface and said second surface, the tab portion bounding the cutting slot, and the tab portion extending from the first portion and the second portion in a direction parallel to axes of the first hole and the second hole.

2. The bone fixation device of claim 1, wherein the first hole is configured for receiving at least a first bone screw for attachment to a first bone segment and the at least one second opening is configured for receiving at least one second bone screw for attachment to a second bone segment.

3. The bone fixation device of claim 1, wherein the first interior end comprises a first cutting surface; and the second interior end comprises a second cutting surface, the first cutting surface and the second cutting surface being substantially parallel to each other.

4. The bone fixation device of claim 3, wherein the first cutting surface and the second cutting surface are substantially perpendicular to the bottom surface of the bone fixation device.

5. The bone fixation device of claim 4, wherein the first cutting surface and the second cutting surface are perpendicular to the first longitudinal dimension and/or the second longitudinal dimension.

6. The bone fixation device of claim 4, wherein the first cutting surface and the second cutting surface are angled relative to a long axis of the bone fixation device.

7. The bone fixation device of claim 3,
   wherein the tab portion extends substantially perpendicularly to the first longitudinal dimension and/or the second longitudinal dimension, and the tab portion has a third longitudinal dimension aligned relative to first longitudinal dimension and/or the second longitudinal dimension.

8. The bone fixation device of claim 1, wherein the tab portion is configured to be at least one of angled or arcuate relative to a top surface of the bone fixation device.

9. The bone fixation device of claim 1, wherein the first portion comprises a third hole.

10. The bone fixation device of claim 1, wherein the second hole is a slot.

11. The bone fixation device of claim 1, wherein the second portion comprises a third hole.

12. The bone fixation device of claim 11, wherein second hole comprise a compression slot and the third hole comprises a compression screw hole.

13. A bone fixation device, comprising:
   a first portion comprising a first surface having a first hole therethrough, a first longitudinal side, a second longitudinal side, and a first interior end closest to a second portion, the first longitudinal side and the second longitudinal side aligned relative to a first longitudinal dimension of the first portion, the first surface bounded by the first longitudinal side, the second longitudinal side, and the first interior end;
   the second portion comprising a second surface having a second hole therethrough, a third longitudinal side, fourth longitudinal side, and a second interior end closest to the first portion, the third longitudinal side and the fourth longitudinal side aligned relative to a second longitudinal dimension of the second portion, the second surface bounded by the third longitudinal side, the fourth longitudinal side, and the second interior end;
   a third portion positioned between the first portion and the second portion, the third portion configured to guide the cutting of a bone;
   the third portion comprising a cutting slot configured to receive a cutting device, the cutting slot bounded only by the first interior end, the second interior end and a third portion connecting portion connecting said first portion and said second portion; and
   the slot comprising a gap between the first portion and the second portion, the gap opposite said connecting portion and providing communication between the slot and an exterior of the slot to allow access to the slot through the gap;
   the first surface and the second surface separated by the slot; and
   wherein the slot is located between the first hole and the second hole in a direction connecting axes of the first hole and the second hole.

14. A bone fixation device, comprising:

a first portion comprising a first surface having a first hole therethrough, a first longitudinal side, a second longitudinal side, and a first interior end closest to a second portion, the first longitudinal side and the second longitudinal side aligned relative to a first longitudinal dimension of the first portion, the first surface bounded by the first longitudinal side, the second longitudinal side, and the first interior end;

the second portion comprising a second surface having a second hole therethrough, a third longitudinal side, a fourth longitudinal side, and a second interior end closest to the first portion, the third longitudinal side and the fourth longitudinal side aligned relative to a second longitudinal dimension of the second portion, the second surface bounded by the third longitudinal side, the fourth longitudinal side, and the second interior end;

a third portion positioned between the first portion and the second portion, the third portion configured to guide the cutting of a bone;

the third portion comprising a cutting slot configured to receive a cutting device, the cutting slot bounded only by the first interior end, the second interior end and a third portion connecting portion connecting said first portion and said second portion; and the slot comprising a gap between the first portion and the second portion, the gap opposite said connecting portion and providing communication between the slot and an exterior of the slot to allow access to the slot through the gap;

the first surface and the second surface separated by the slot; and wherein the first hole and the second hole have axes extending parallel to a direction of a transverse dimension of said third portion connecting portion.

* * * * *